United States Patent [19]

Jirikowski

[11] Patent Number: 5,424,219
[45] Date of Patent: Jun. 13, 1995

[54] METHOD OF PERFORMING ASSAYS FOR BIOMOLECULES AND SOLID SUPPORTS FOR USE IN SUCH METHODS

[75] Inventor: Gustav F. Jirikowski, San Diego, Calif.

[73] Assignee: Cytech Biomedical, Inc., Sarasota, Fla.

[21] Appl. No.: 782,934

[22] Filed: Oct. 25, 1991

[51] Int. Cl.⁶ ............... G01N 33/543; G01N 33/545
[52] U.S. Cl. ........................... 436/518; 435/4; 435/6; 436/531; 436/800; 436/805; 436/807; 436/809; 522/1; 528/491; 528/494; 528/495; 528/497; 528/498; 528/502 R
[58] Field of Search ............... 528/491, 494, 495, 497, 528/498, 502; 156/654, 668; 435/4, 6; 436/518, 531, 800, 805, 809, 807; 522/1

[56] References Cited

U.S. PATENT DOCUMENTS

| | | | |
|---|---|---|---|
| 3,639,516 | 2/1972 | Sarfaty et al. | 260/818 |
| 3,663,325 | 5/1972 | Uda et al. | 156/668 |
| 3,666,733 | 5/1972 | Epton | 260/80 |
| 3,700,609 | 10/1972 | Tregear | 260/2.5 |
| 3,847,745 | 11/1974 | Axen et al. | 195/68 |
| 3,898,087 | 8/1975 | Brutchen et al. | 522/65 |
| 3,966,580 | 6/1976 | Janata et al. | 204/195 |
| 4,001,583 | 1/1977 | Barrett | 250/303 |
| 4,119,589 | 10/1978 | Horn et al. | 260/6 |
| 4,197,361 | 4/1980 | Hoff et al. | 424/8 |
| 4,210,418 | 7/1980 | Brown et al. | 23/230 |
| 4,217,338 | 8/1980 | Quash | 424/1 |
| 4,235,867 | 11/1980 | Thoma | 436/531 |
| 4,248,965 | 2/1981 | Mochida et al. | 436/531 |
| 4,450,231 | 5/1984 | Ozkan | 435/7 |
| 4,588,680 | 5/1986 | Bucher et al. | 435/5 |
| 4,681,782 | 7/1987 | Ozkan | 436/809 |
| 4,820,644 | 4/1989 | Schafer et al. | 436/518 |
| 4,933,410 | 6/1990 | Okrongly | 525/333.6 |
| 4,998,284 | 3/1991 | Bacus et al. | 358/101 |
| 5,160,600 | 11/1992 | Patel et al. | 156/668 |

FOREIGN PATENT DOCUMENTS

| | | |
|---|---|---|
| 0026007 | 4/1981 | European Pat. Off. |
| 0133272 | 2/1985 | European Pat. Off. |
| 0219695 | 4/1987 | European Pat. Off. |
| 0345027 | 12/1989 | European Pat. Off. |
| 0410323 | 1/1991 | European Pat. Off. |
| 0422599 | 4/1991 | European Pat. Off. |
| 0442231 | 8/1991 | European Pat. Off. |
| 2738183 | 3/1978 | Germany. |

OTHER PUBLICATIONS

Webster, Owen W., "Science", vol. 251, 1991, pp. 887-893.
Bates, F. S., "Science", vol. 251, 1991, pp. 898-905.
Stanley et al, "Enzyme Amplification can Enhance Both Speed & Sensitivity of Immunoassays", J. Immunol. Meth., vol. 83, pp. 89-95, (1985).
Week 8716, Derwent Publications Ltd., London, GB; AN 87-111859 & JP,A, 62 056 862 (Kanebo KK) Mar. 12, 1987.
Patent Abstracts of Japan, vol. 7, No. 160 (P-210) (1305) Jul. 14, 1983 & JP,A, 58 70 164 (Toyo Boseki K.K.) Apr. 26, 1983.

(List continued on next page.)

*Primary Examiner*—Toni R. Scheiner
*Assistant Examiner*—Christopher L. Chin
*Attorney, Agent, or Firm*—Robert M. Schwartz; Edward I. Mates

[57] ABSTRACT

Methods of performing an assay for biomolecules and solid supports for use in such assays are disclosed. An activated polymeric material is used as a solid support for binding biomolecules. In a preferred form, the support is made of a generally hydrophobic, nonporous polymer which has been activated by treatment with solvents or by mechanical means to enhance the binding characteristics of the support. The support can be made of a copolymer, such as a copolymer of polystyrene and polybutadiene. Detection of bound biomolecules is preferably performed by means of staining reactions and gray level scanning. Emulsifying agents, such as detergents, can be applied to the surface of the support to substantially inhibit additional materials from being bound to the support.

19 Claims, 1 Drawing Sheet

OTHER PUBLICATIONS

Journal of Immunological Methods. vol. 83, Oct. 24, 1985, Amsterdam pp. 55–60, M. Sarkar et al. 'Immobilization Of Antibodies On A New Solid Phase For Use In Elisa'.

J. D. Sedgwick, et al., "A solid phase immunoenzymatic technique for the enumeration of specific antibody secreting cells," J. Immunol. Meth., vol. 57, pp. 301–309 (1983).

S. F. De St. Groth, "The evaluation of limiting dilution assays," J. Immunol. Meth., vol. 49, pp. R11–R23 (1982).

E. Macy et al., "Enhanced ELISA: How to measure less than . . . 8 hours," F.A.S.E.B. Journal, vol. 2, pp. 3003–3009 (1988).

METHOD OF PERFORMING ASSAYS FOR BIOMOLECULES AND SOLID SUPPORTS FOR USE IN SUCH METHODS

FIELD OF THE INVENTION

This invention relates generally to methods of performing assays for biomolecules using polymeric supports, and is particularly directed to assay methods using polymeric supports which have enhanced binding characteristics.

BACKGROUND OF THE INVENTION

Immunoassay is a class of scientific techniques used to detect small amounts of biomolecules in biological samples. These techniques are widely used in medical diagnostic procedures, such as blood tests and the like, to detect specific proteins ("antigens"). Conventional methods of immunoassay rely on the selective reaction of a particular protein with an antigen. For example, it is well known that animals develop a specific antibody to combat a particular foreign antigen. Because the antibody has a highly specific chemical configuration, it reacts selectively with the antigen and not with other proteins. The reaction of the antibody with the antigen ("precipitation") binds the antigen so that it can be further processed and, ultimately, destroyed or removed from the system. Such antibody-antigen reactions give rise to the well-known immune response in animals, by which animals are able to resist infections to which they have been previously exposed.

This ability of antibodies to selectively bind to antigens can also be used to detect antigens present in a biological sample. For example, when a patient has a particular illness, one or more characteristic antigens will be present in the blood. An antibody to that antigen will selectively bind to the antigen. A common type of immunoassay which relies on this effect is the "antibody capture assay." To detect an antigen in a particular sample, the antigen is first immobilized by attaching it to a solid support. A support often used for this purpose is a "microtiter plate," which is a plastic plate made of clear polystyrene or polyvinylchloride. The plate is molded with 96 depressions or wells in which biological samples are held for testing. When a sample is added to a well in the plate, antigens in the sample are bound or attached to the support, and are thereby immobilized. This binding is not a chemical reaction but, rather, is believed to result from a physical or noncovalent interaction between the polystyrene matrix and the antigen.

Once the antigen is bound to the support, an antibody known to be specific to that antigen is allowed to react with, and bind to, the immobilized antigen. It is then possible to detect the presence of the antigen indirectly by detecting the antibody bound to the antigen. This is accomplished by "labelling" the antibody. One way antibodies are labelled is with a radioactive isotope, which is incorporated into the molecular structure of the antibody, and can be detected using known detection systems.

Another commonly used labelling method is to bind a second antibody to the first antibody. This second antibody is linked with a "marker" enzyme, such as horseradish peroxidase. A dye which is substantially water-insoluble and changes color in the presence of the marker enzyme is added to the solution. Thus, if sufficient antigen is bound to the walls of the microtiter plate, it is possible to detect the antigen by the color change which occurs when the dye reacts with the marker enzyme.

Within limits, it is also possible to determine how much antigen is present by measuring the intensity of this color change. One well known technique which relies on this effect is ELISA (Enzyme Linked Immunosorption Assay). With ELISA, the amount of antigen present is determined by measuring the amount of color change in the wells of the microtiter plate using a photometer known as an "ELISA reader." A detailed description of ELISA techniques can be found in E. Macy, et al., "Enhanced ELISA: How to measure less than 10 picograms of a specific protein in less than 8 hours, . . . "F.A.S.E.B. Journal, Vol 2, pp. 3003–009 (1988), and S. F. De St. Groth, "The evaluation of limiting dilution assays," J. Immunol. Meth., Vol. 49, pp. R11–R23 (1982), both of which are incorporated herein by reference and made a part hereof.

Because ELISA is based on measuring the color change caused by the reaction of a dye with the marker enzyme in a solution, it has limited sensitivity. When small amounts of antigen are present, the color change is so slight that it can be lost in the background "noise" of the measurement system. Noise is created when excess antibodies or marker enzymes bind directly to the walls of the support. When the dye is added, these materials cause a color change which is not related to the amount of antigen present. In addition, once a certain amount of color change occurs, further color change is difficult to detect, making the assay less than ideal for quantifying larger amounts of antigen.

Most significantly, because ELISA relies on the detection of light which passes through the stained solution, only clear supports—which do not interfere with the passage of light—can be used to bind the antigen. The need for a transparent support places limitations on the surface characteristics of the support materials which may be used for ELISA and similar assays. Thus, if a particular support material does not have the desired optical transparency, it cannot be used, even if it has better antigen binding properties.

To date, attempts to increase the sensitivity of ELISA have concentrated on increasing the binding capacity of the support without diminishing its optical transparency, so that the sample can be analyzed photometrically. Several such attempts have been directed to changing the chemical configuration of the surface so that it will form a chemical bond with the antigen. For example, U.S. Pat. No. 4,933,410 to Okrongly discloses activating polystyrene supports by reacting the surface of the support with hydroxymethylamides in a polystyrene insoluble solvent. It is recommended that this activation take place under mild conditions in a solvent which neither dissolves nor swells the polystyrene to maintain the optical clarity of the support. Similarly, U.S. Pat. No. 4,119,589 discloses activating a compound having at least two secondary amine groups by converting the secondary amine groups into imino-chloride groups.

It has also been proposed to add a coating to the surface of the support to bind the protein. For example, U.S. Pat. No. 4,210,418 to Brown, et al. discloses coating the support with an inert protein which binds the antigen by adsorption, ionic binding, entrapment or, more preferably, covalent binding. To facilitate attachment of the inert protein, the surface of the support may be treated with materials, including solvents, surfactants, acids, or bases, to enhance adsorption. (See U.S. Pat. No. 4,210,418, col. 5, lns. 12–16.)

The binding of biomolecules such as antigens to solid supports has three basic components: capacity, affinity, and stability. Capacity is the maximum amount of material that can be bound per surface area of support. Affinity is the degree of attraction between the antigen and the support. Stability is the level of permanence of the bond between the biomolecule and the support. While the affinity and stability of binding is thought to be an inherent feature of the particular polymeric material being used, capacity can be enhanced by activation processes.

The methods of activating supports described above have focused on changing the surface properties of the support in an effort to increase binding capacity. However, merely increasing binding capacity does not ensure that the support will be better for immunoassay. For example, if the stability of binding is low, the bound biomolecules will tend to bleed off during biochemical analysis, decreasing the sensitivity of the analysis. Likewise, if the affinity of the support is low, binding will be too slow—a disadvantage for analytical procedures.

Other supports currently used for immunoassay include porous membranes made of nitrocellulose, nylon, and similar materials. These materials are porous and hydrophilic, that is, they tend to bind or absorb water. The use of such hydrophilic materials is thought to increase binding capacity by drawing water (in which the biomolecules are carried) into the support. Although such supports have improved binding characteristics, they suffer from several drawbacks. First, because these materials are hydrophilic, samples blotted onto such supports spread and do not remain on the surface of the support. Therefore, it is difficult to saturate free binding sites on the support. Antibodies, dyes, and other materials used for detection can bind to these available sites, resulting in false readings or background staining. Also, because these supports are hydrophilic, washing does not remove these materials as completely or efficiently; as a result, it is more difficult to accurately quantify the amount of a particular biomolecule that is present.

Accordingly, it is an object of the present invention to provide a method of performing an assay for biomolecules which is more accurate than conventional methods.

It is a further object of the invention to provide an assay method which can be performed using readily available materials and comparatively inexpensive detection equipment.

It is a further object of the invention to provide an assay method in which biomolecules can be detected using water-insoluble dyes.

It is a further object of the invention to provide an assay method in which background staining and resultant noise can be significantly reduced, thereby increasing the accuracy and sensitivity of the assay.

It is a further object of the invention to provide an assay method which can be relatively easily performed with a minimum of labor-intensive steps.

It is a further object of the invention to provide an assay method using solid supports which do not have to be optically transparent.

It is a further object of the invention to provide a solid support for use in detecting the presence of biomolecules which has improved binding capacity and affinity.

It is a further object of the present invention to provide a solid support which is not hydrophilic so that the binding of biomolecules to the support may be carefully controlled.

It is a further object of the invention to provide a solid support which is made using readily available, inexpensive materials and relatively simple production processes.

SUMMARY OF THE INVENTION

These and other objects are accomplished by providing a method of performing an assay for biomolecules in which an activated polymeric material is used as a solid support for binding biomolecules. In a preferred form, the support is made of a generally hydrophobic, nonporous polymeric material and has a region which has been activated by increasing the exposed surface area of the support. Activation can be accomplished by treating the support with solvents to partially dissolve the support or by mechanical means.

Biomolecules to be detected are bound to the activated region of the solid support, and are detected once they are bound to the support. Detection can be performed by means of staining reactions and gray level scanning, thus obviating the need to use transparent supports. In addition, because of the enhanced binding characteristics of such supports, the accuracy and sensitivity of the assay is substantially enhanced.

In another embodiment of the invention, an emulsifying agent, such as a detergent, is applied to the surface of the solid support after the biomolecule is bound. Such emulsifying agents substantially inhibit additional materials from being bound to the support, thereby significantly reducing background reactions and further increasing accuracy and sensitivity.

In a further embodiment, the solid support is comprised of a copolymeric material, such as a copolymer of polystyrene and butadiene. It is preferred that such supports be activated; however, it has been found that supports made of copolymers have enhanced binding characteristics even in an unactivated condition.

A further aspect of the present invention is the specially designed solid supports useful in performing the assays of the present invention. Preferably, such supports are made of a polymeric material and have an activated region for binding a biomolecule to be detected. In a further preferred form, the support is made of a copolymer and can be used either in an activated or an unactivated condition. The support can be formed in any number of desired shapes, including a substantially flat plate, a reaction vessel, beads or granules, a thin foil, or a fibre.

The foregoing features and advantages of the present invention will be readily understood upon consideration of the following detailed description, taken in conjunction with the accompanying drawings, in which:

DETAILED DESCRIPTION

Figure 1:
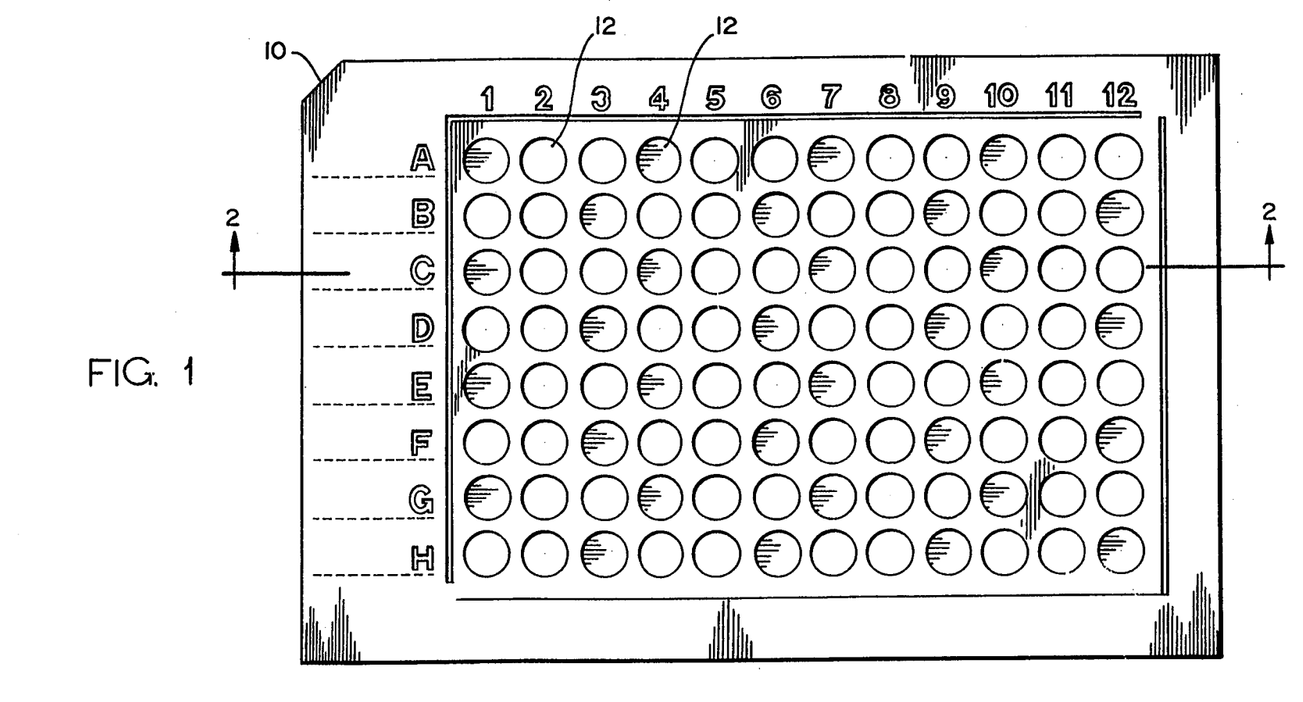
FIG. 1 is a top view of a solid support made in accordance with aspects of the present invention.
Figure 2:
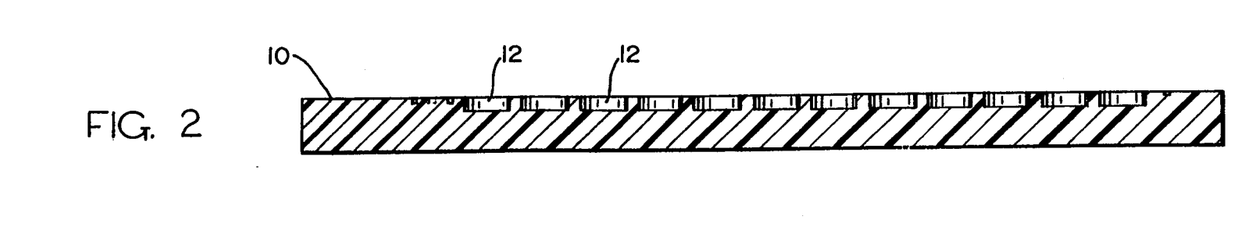
FIG. 2 is a cross-sectional view of the solid support illustrated in FIG. 1 taken along the line 2—2 in FIG. 1.

The assay methods of the present invention are designed to detect biomolecules, such as, by way of example, proteins, peptides, polypeptides, nucleic acids, nucleotides, polynucleotides, amino acids, monoamines, polysaccharides, lipopolysaccharides, and the like. To perform the assay, a specially-designed solid support material is used. FIGS. 1 and 2 illustrate a solid support generally made in accordance with the present invention, which has been formed in the shape of a substantially flat plate 10. The plate 10 has a total 96 depressions 12 formed therein for receiving biological samples containing biomolecules.

In general, supports useful in the practice of the present invention are made of a solid polymeric material which is either transparent or opaque. Preferably, the polymeric material is generally hydrophobic and nonporous so that the binding of biomolecules and other reagents can be more readily controlled. By way of example, suitable polymeric materials include polymers and copolymers of polystyrene, polypropylene, polybutadiene, polyvinylchloride, polyamide, polycarbonate, epoxides, methacrylates, and polymelamine. For the reasons discussed below, supports made of copolymers of styrene and butadiene are particularly preferred in the practice of the present invention.

For a number of reasons, it is particularly desirable that the polymeric material be hydrophobic, that is, water repellant. Hydrophobic materials are more easily coated with detergents. As discussed in greater detail below, this makes it possible to inhibit binding on the surface of the support (e.g., to minimize binding of detection reagents), by coating the support with detergent. Thus, addition or omission of detergents makes it possible to control the binding of biomolecules. The use of hydrophobic materials also makes washing steps far more efficient.

The support may be molded from the polymeric materials by conventional methods of injection molding. However, it will be understood that other well-known methods of forming the support may also be used, such as, by way of example, compression molding, blow molding, extrusion, and the like. In general, however, injection molded supports have been found to be preferable to date, since the injection molding process tends to give the surface of the support a "matte-type" or "grainy" finish, particularly when the mold is sand-blasted prior to use. This grainy surface is believed to provide more available binding sites for biomolecules and to enhance binding by reducing the cohesion of solutions carrying biomolecules. It is also possible to impart a roughened surface to the support by other mechanical methods, such as grinding, sanding, and the like.

The support is preferably provided with one or more regions that have been "activated." Such activation is designed to increase the exposed surface area of the support and, even more preferably, to open the polymer matrix. In this way, the support has an improved capacity and affinity for binding biomolecules, and the resulting bonds have more stability. It should be noted that this binding is believed to be a mechanical or physical binding between the support surface and the biomolecule, not a chemical bond.

Preferably, the polymeric material is activated by treating the surface of the support with one or more solvents. Preferred solvents are materials which partially dissolve, erode, or abrade the polymer molecules on surface of the support, thereby opening the polymer matrix and making the polymer matrix available for binding with the biomolecule. Solvents which may be used for this purpose include ethers, alcohols, ketones, aldehydes, acids, bases, olefins, linear and cyclic hydrocarbons, halogenated hydrocarbons, and similar materials which partially dissolve the support constituent(s).

As described above, it is also possible to activate the surface of the support by mechanical means, such as grinding, sanding, and the like, or by injection molding the support in a mold which has been roughened by sand-blasting, as noted above. While such mechanical methods are not believed to change the polymer matrix at a molecular level, they do improve binding by increasing the available surface area of the support and, it is believed, by changing the cohesion of aqueous solutions on the surface of the support. In addition, particularly when emulsifying agents are used to inhibit further binding, as described below, it is possible to use supports which have not been activated.

When applied to the surface of the support, solvents tend to "roughen" the surface and thereby increase the surface area of the support which is exposed to samples coming in contact with it and which is available for binding; it is also believed that solvents open the polymer matrix at a molecular level, thereby further enhancing binding capacity. Rigorous treatment with solvents may make the support opaque to the passage of light. Although opaque supports have previously been viewed as inferior to transparent ones, it has been discovered that the ability of light to pass through the support is not critical when the proper detection systems are used, as explained below.

To activate one or more regions on the solid support, the support may be dipped or soaked in the solvent for a period of time sufficient to roughen the surface of the support and thereby open the polymer matrix. Alternatively, the solvent may be applied to the support by spraying, painting, or otherwise applying the solvent onto the support. The amount of time required for activation varies depending upon the particular solvent and polymer system being used. However, for most applications, activation can be accomplished within about 1 minute. Within limits, more prolonged solvent treatments tend to give substrates with enhanced binding characteristics.

Polymeric materials which are particularly preferred for use as solid supports are copolymers of two or more polymers which are differently affected by the activation process. For example, the solvent acetone quickly dissolves polystyrene, but does not dissolve butadiene as readily. Accordingly, when a copolymer of polystyrene and butadiene (a high-impact polystyrene) is treated with acetone, the polystyrene component is readily dissolved, while the butadiene component is not. This is believed to result in a substantial enhancement of the binding properties of the polymeric support by exposing the sticky, resinous polybutadiene component of the copolymer. The total binding capacity of supports made of such copolymers, as well as their binding affinity and the stability of the resulting bonds, is thereby substantially increased. For a general description of copolymers and their characteristics, the reader is referred to O. W. Webster, "Science," Vol. 251, pp. 887-93 (1991), and F. S. Bates, "Science, "Vol. 251 pp 898-905 (1991), both of which are incorporated herein by reference and made a part hereof.

It has also been discovered that supports made of suitable copolymers may be used in an unactivated condition to bind biomolecules. Because of the unique binding properties of copolymeric materials, and particularly copolymers of styrene and butadiene, activation, while preferred, is not necessary, and suitable results may be obtained simply by using unactivated surfaces of such copolymeric supports for binding. In addition, other copolymers, such as copolymers of the polymers listed above, may also be used in this manner.

The solid supports of the present invention are provided for use in a method of performing an assay for biomolecules, including proteins, amino acids, peptides, polypeptides, proteins, nucleic acids, amines, amino acids, monoamines, nucleotides, polynucleotides, polysaccharides, lipopolysaccharides, and the like. A sample of a biological material containing a particular biomolecule to be detected is transferred onto one or more of the activated regions on the solid support. In the support illustrated in FIGS. 1 and 2, the plate 10 is molded with a plurality of depressions 12 so that each sample can be physically separated from the others. In a preferred form, the depressions 12 are activated by one or more of the chemical or mechanical methods described above, while the remainder of the plate is left with a shiny, polished surface. In this way, samples spread and bind within the activated depressions, but tend to cohere or bead up on the shiny, raised surface of the plate. This helps to prevent samples from spreading when they are placed on a non-activated region and thereby potentially contaminating samples in another depression. By maintaining the sample in contact with the activated region of the support for an incubation period, the biomolecules in the sample become bound to the support, at which point they can be qualitatively and quantitatively analyzed.

In a preferred method of carrying out the assay of the present invention, the physical bond between the biomolecules and the support can be enhanced by creating additional covalent links within the polymer matrix to cause covalent binding of biomolecules to the activated solid support. This can be accomplished by exposing the support to ultraviolet light after the biomolecules are attached to the support surface. Ultraviolet light changes the surface of certain polymers by accelerating the polymerization of the polymer. Polymers which are affected in this manner include polystyrene, epoxides, methacrylates, and polymelamine. Upon treatment with ultraviolet light, the surface of the support is partially polymerized, thereby enhancing cross-linking of the polymer and embedding or capturing the bound biomolecules within the cross-linked support matrix. These additional covalent links increase the stability of the bond between the biomolecules and the support. It will also be understood that other methods of providing enhanced cross-linking within the polymer matrix, such as treatment with formaldehyde, glutaraldehyde, picric acid, and acrolein, may also be used to enhance the stability of the bond.

Once the biomolecule is bound to the activated region of the support, various means may be used to detect the presence and amount of biomolecules bound. In protein or enzyme assays, the bound biomolecules may be stained right on the surface of the support. The degree of staining can then be measured using gray level scanning. When using immunoenzymatic assay or hybridization techniques, the reaction products may also be made visually apparent by applying water insoluble dyes on the surface of the plate. Preferred dyes include Naphtol-AS-BI phosphate/new fuchsin (NABPNF), 3'3-diaminobenzidene, 4-chloro-1-naphtol, 9-amino-9-ethylcarbacol, colloidal gold, and other materials well known to those skilled in the art.

In the practice of the present invention, the use of water insoluble dyes to visualize the presence of the biomolecules or reaction products on the support is preferred. Because the support is hydrophobic, water insoluble dyes tend to remain on the surface of the support and resist spreading or leaching off into the solution within the vial. This is believed to further improve the accuracy of the assay by concentrating the staining reaction in the vicinity of the biomolecule or reaction products. However, although water insoluble dyes are preferred, it will be understood that suitable water soluble dyes and other indicators may also be used.

Particularly when using immunoenzymatic and hybridization assay techniques, it is desirable to saturate free binding sites on the support prior to detection so that the detection systems used to indicate the presence of antigen, or other biomolecules, do not bind to these free sites and cause background staining when the staining reaction takes place. Suitable materials which may be used for this purpose are well known to those skilled in the art and include bovine serum albumine (BSA), as well as salmon sperm DNA, poly L-lysin, and clysin.

In a further embodiment of the present invention, it is preferred to substantially prevent or inhibit further binding to the support once the desired biomolecules have been bound. To achieve this, it has been discovered that it is desirable to rinse the support with an emulsifying agent, such as a detergent solution, to substantially inhibit further binding prior to detection. Detergents are generally not bound to the polymeric support. However, they change the cohesion of water so that they coat all substances present, including biomolecules, materials used to saturate free binding sites, and the polymeric support, with a hydrate layer. This effect substantially inhibits the ability of detection reagents and other biomolecules to bind to the support, thereby reducing background staining. Other emulsifying agents, such as, by way of example, Triton X100 (octyl phenoxy polyethoxyethanol), Tween 20 (polyoxyethylenesorbiton), SDS (sodium dodecylsulfate), ionic and anionic tensides, borates, and soaps, may also be used for this purpose.

It has been discovered that conventional gray level scanners and software may be used in detecting the intensity of staining or labelling for biomolecules and reaction products. Success has been had with a gray level scanner manufactured by Macintosh (model "Abaton SCII"), used in conjunction with a Macintosh IIA/UX computer and "Abaton DA" software. Quantification has been successfully accomplished using "Image 1.31" software available free of charge to laboratories from Wayne Respend of the National Institute of Mental Health, Bethesda, Md. It is also possible to provide software which is specifically designed for gray level reading of supports having multiple wells or depressions. Such a program is preferably designed to locate preset or adjustable coordinates, specify an area around the coordinate (fully adjustable by radius, cross hair, or square), and measure the gray level of that area for quantification. Also, such a program preferably has fully adjustable grid screens to allow simultaneous scanning and quantifying of up to 192 fields. The program preferably reads the supports directly when staining methods are used, or reads x-ray film when autoradiographic quantification is used.

It will be understood by those skilled in the art that the use of gray level scanning in detection may place some limitations on the depth of depressions in the surface of the support used to hold samples, since the walls of the depressions cast a shadow into the interior of the depression, thereby interfering with gray level analysis. For example, in the plate illustrated in FIGS. 1 and 2, the depressions are kept to an approximately 0.008 inch depth or less so that the shadow does not interfere with scanning. Naturally, this concern becomes less significant as the diameter of the depression increases.

Of course, it will be understood that other well known methods of detecting the biomolecules may also be used in the practice of the present invention. For example, it is also possible to use radioactive detection methods, autoradiography, and scintillation counting for purposes of detection. A support carrying immobilized radioactive samples can be dissolved in scintillation fluid, xylene, toluene, benzene, or the like, for scintillation counting. This approach is especially desirable when isotopes which emit low intensity radiation, such as tritium or carbon-14, are used.

The solid supports of the present invention may be formed into any number of useful shapes for use in detecting or binding biomolecules in immunoassay. In general, the support should be formed to permit the use of conventional detection systems. For example, the support may be formed in the shape of a substantially flat plate. Such a plate may be formed with a grid of depressions for separating samples, i.e., in the general shape of a microtiter plate, as shown in FIGS. 1 and 2. Likewise, the plate may simply be substantially flat but without depressions formed therein. Such a plate is useful, for example, in performing hybridization techniques well known to those skilled in the art. In that event, it is particularly preferred that the plate be activated completely on one side and left with a shiny, unactivated surface on the other, thereby facilitating hybridization techniques. The support may also be formed in the shape of a vessel, such as a reaction tube, or as beads or granules of a substrate which can bind or capture biomolecules. The support may also be formed as a thin foil of polymeric substrate or as fibers or strands. Particularly when the support materials are formed as beads, granules, fibers, strands, and the like, they have utility as filtering media for biomolecules, in addition to use in assays.

There are several significant advantages to the assay methods and supports of the present invention. First, because staining reactions preferably occur right on the surface of the solid support, rather than in a solution within the vial, the assays of the present invention are substantially more sensitive than conventional immunoassays, such as ELISA. Second, gray-level scanners, which are relatively inexpensive when compared with photometers (ELISA readers), may be used for detection. Third, because detection does not need to rely on photometric measurements, opaque supports, which have been activated to give them enhanced binding characteristics, may be used. Fourth, because the carrier material is preferably hydrophobic, washing steps are more efficient than conventional blot preparations using nitrocellulose or nylon membranes. Finally, the inhibitory action of detergents on binding makes the support much more efficient than other support systems.

The following specific examples are illustrative of the methods and materials which may be used in the practice of the present invention and are provided solely to illustrate some of the ways the invention may be practiced:

EXAMPLE 1

PROTEIN ASSAY

A white plate of injection molded copolymer of polystyrene and polybutadiene similar to that shown in FIGS. 1 and 2 is activated by soaking for 10 sec. in acetone and air dried thereafter. A dilution series of bovine serum albumine (BSA), ranging from 10 g/l to 1 fg/l, is applied as single drops, 15 $\mu$l each, to the activated carrier. The plate is incubated in a humid chamber for 2 hrs. Excess liquid is removed thereafter by blotting on filter paper. The plate is then stained in Coomassie blue (250 mg of Coomassie blue in 45% methanol and 10% acetic acid) for 10 min. Thereafter, the plate is rinsed with water and air dried. The intensity of staining is evaluated with a computer scanner and a gray level measuring program. The results are presented in the form of a histogram. The lowest sensitivity level of this method is as low as 10 pg/l.

The present method is far simpler than common protein assay methods (e.g. the Lowry method) and is far more sensitive.

EXAMPLE 2

ENZYME ASSAY

A solution containing an enzyme to be measured (e.g.. alkaline phosphatase in a plasma sample) is pipetted in single drops onto a support like that described in Example 1 which has been sprayed with 100% isopropanol and dried prior to use. Samples are allowed to bind to the plate in a humid chamber for 1 hr. Excessive material is removed by blotting onto filter paper. The plate is then immersed in a solution of Naphtol-AS-BI phosphate/new fuchsin (NABPNF) for 30 min. The staining reaction is then stopped with 20 mM EDTA. The plate is then washed in water, dried, and quantified as in Example 1.

EXAMPLE 3

IMMUNOENZYMATIC QUANTIFICATION OF PEPTIDE HORMONES

Samples to be tested, as well as a dilution series of the synthetic peptide for a standard curve, are pipetted (as in Example 1) onto an opaque polystyrene plate that has been activated by immersion in 100% ethanol. After binding in a humid chamber for 2 hrs., excess fluid is removed by blotting. Free binding sites on the plate are saturated by immersing the entire plate in 5% BSA for 30 min. Thereafter, the plate is rinsed in phosphate buffer containing 0.05% Triton×100 (PBS). An antibody against the peptide to be detected is diluted in PBS 1:1000 and applied to the plate for 2 hrs. The plate is Washed again in PBS and subsequently incubated with a secondary antibody, which is directed against the species of the first antibody and which is labelled with peroxidase. This incubation step takes 30 min. at room temperature. After 3 washing steps, the plate is stained in a freshly prepared solution containing 12 mg diaminobenzidine, 10 $\mu$l of a 30% hydrogen peroxide solution and 200 $\mu$l of a nickel chloride solution, all dissolved in 100 ml PBS. The staining reaction takes about 10 min. and is self-terminating. The plates are rinsed in water and dried. The intensity of staining is then quantified with a scanner as described above.

Similar immunoassays are currently performed as enzyme linked immunosorption assays (ELISA), which are approximately 1000 times less sensitive than the present method due to the fact that the immunoprecipitates and marker enzymes are attached to the walls of a microtiter plate, and the reaction product is generated in a solution within the vial. Moreover, when using ELISA, the reaction has to be carefully timed and stopped to control nonspecific reactions.

For immunoenzymatic assays such as that described in Example 3, the present invention represents a significant improvement with respect to sensitivity. Since the carrier is water repellent, and the binding of substances can be inhibited to nearly 100% by the presence of detergents, background reactions are completely absent, resulting in an excellent signal to noise ratio. This makes the entire arsenal of immunochemical amplification techniques available, resulting in very high sensitivity levels. For a general discussion of the amplification techniques which may be used, the reader is referred to J. D. Sedgwick, et al., "A solid phase immunoenzymatic technique for the enumeration of specific antibody secreting cells," J. Immunol. Meth., Vol. 57, pp. 301-09 (1983), S. F. De St. Groth," The evaluation of limiting dilution assays," J. Immunol. Meth., Vol. 49, pp. R11-R23 (1982), and C. J. Stanley, et al , "Enzyme amplification can enhance both speed and sensitivity of immunoassays, "J. Immunol. Meth., Vol 83, pp 89-95 (1985), all of which are incorporated herein by reference and made a part hereof.

EXAMPLE 4

DOT-BLOT TO DETERMINE mRNA

A sterile plate, similar to that illustrated in FIGS. 1 and 2, is loaded with samples containing RNA extracts, as well as a dilution series of synthetic RNA as a standard. After binding and blotting as described above, the plate is saturated with 100 μg/ml of salmon sperm DNA. The plate is then exposed to UV light for 10 min. to facilitate cross-linking of the surface of the support. Thereafter, the plate is incubated with a synthetic oligonucleotide probe radiolabeled or antigen labeled, complementary to the sequence of RNA to be analyzed. Hybridization takes place within 1 hr. at 37° C. in a humid chamber. The hybridization buffer contains 0.05% Tween 20, and the concentration of the probe is 5 pM/ml. Thereafter, the plate is washed in PBS at a temperature 5° C. below the dT of the used probe. The plate is then dried and exposed to X-ray film for autoradiography (when a radioactive probe is used) or developed for immunodetection of the nonradioactively labelled probe, as described in Example 3. X-ray films as well as immunostained plates are quantified as described above.

Thus far, nitrocellulose or nylon membranes have been used primarily for dot-blots. The disadvantages of such carriers are that they are hydrophilic and porous. Samples which are blotted onto such supports spread and do not stay on the surface of the carrier. Therefore, it is difficult to saturate free binding sites, resulting in higher background staining. This, in turn, accounts for an unfavorable signal to noise ratio and lower sensitivity. The water repellent material used in the Example 4 has nearly no background, due to the action of detergents.

While the invention has been described in connection with certain preferred embodiments, those skilled in the art will recognize many modifications to structure, arrangement, portions, elements, materials, steps, and components which can be used in the practice of the invention without departing from the principles thereof.

What is claimed is:

1. A method of performing an assay for biomolecules in a sample comprising:
   providing a solid support of polymeric composition consisting essentially of at least two suitable polymeric components selected from the group consisting of polymers and copolymers, said suitable polymeric components capable of dissolving at different rates when exposed to a solvent composition, so that one of said suitable polymeric components dissolves more quickly and the other of said suitable polymeric components dissolves less readily when said solid support is exposed to said solvent composition,
   exposing said solid support to said suitable solvent composition in a region of said solid support to remove a portion of the polymeric components in said region with said solvent composition to increase the exposed surface area of the region,
   contacting the sample to said solid support and allowing binding region of the solid support,
   removing any excess sample from the solid support,
   contacting the solid support with a detectable reagent that specifically binds to the biomolecules,
   removing excess detectable reagent from the solid support, and
   detecting the detectable reagent on the solid support to determine the presence of biomolecules bound to said region of the solid support.

2. The method of claim 1 in which the solid support has been activated by treating said region with an organic solvent to partially dissolve the polymeric material.

3. The method of claim 2 in which the solvent is selected from the group consisting of ethers, alcohols, ketones, aldehydes, acids, bases, olefins, linear and cyclic hydrocarbons, and halogenated hydrocarbons.

4. The method of claim 1 in which the polymeric composition comprises a member selected from the group consisting of polystyrene and polyvinylchloride.

5. The method of claim 1 in which the polymeric composition is a copolymer of styrene and butadiene.

6. The method of claim 1 in which the activated region is opaque.

7. The method of claim 1 in which the biomolecule is detected by using a staining dye to indicate the presence of the biomolecule and using gray level scanning to measure the intensity of staining.

8. The method of claim 1 in which the biomolecule is detected by using a substantially water-insoluble staining dye.

9. The method 1 in which the biomolecule is a member selected from the group consisting of proteins, nucleic acids, amino acids, peptides, amines, and nucleotides.

10. The method of claim 1 in which the biomolecule is covalently bound to the surface of the activated region of the support after binding the biomolecule.

11. The method of claim 10 in which the biomolecule is embedded in the activated region of the support by exposing the activated region of the support binding the biomolecule to ultraviolet light.

12. The method of claim 1 in which the support is formed in the shape of a substantially flat plate.

13. A method of performing an assay for biomolecules as in claim 1 comprising:

subsequently applying an emulsifying agent to the surface of the solid support after the biomolecule is bound to the solid support to substantially inhibit additional materials from being bound to the support.

14. The method of claim 13 in which the polymeric material comprises a member selected from the group consisting of polypropylene, polystyrene, polyvinylchloride, polyamide, polycarbonate, epoxides, methacrylates, and melamine resin.

15. The method of claim 13 in which the polymeric material is a copolymer.

16. The method of claim 15 in which the polymeric material is a copolymer of styrene and butadiene.

17. The method of claim 13 in which the emulsifying agent is a detergent.

18. The method of claim 13 in which the biomolecule is detected by using a staining dye to indicate the presence of the biomolecule and using gray level scanning to measure the intensity of staining.

19. The method 13 in which the biomolecule is a member selected from the group consisting of proteins, nucleic acids, amino acids, peptides, amines, and nucleotides.

* * * * *

UNITED STATES PATENT AND TRADEMARK OFFICE
CERTIFICATE OF CORRECTION

PATENT NO. : 5,424,219

DATED : June 13, 1995

INVENTOR(S) : Gustav F. Jirikowski

It is certified that error appears in the above-identified patent and that said Letters Patent is hereby corrected as shown below:

Col. 12, line 23, after "binding" insert --of biomolecules to said--.

Signed and Sealed this

Twelfth Day of December, 1995

Attest:

BRUCE LEHMAN

Attesting Officer

Commissioner of Patents and Trademarks